United States Patent [19]
Galley et al.

[11] Patent Number: 5,688,492
[45] Date of Patent: Nov. 18, 1997

[54] ORAL HYGIENE COMPOSITION

[75] Inventors: Edward Galley; Michael David Cooper, both of Nottingham, England

[73] Assignee: The Boots Company PLC, Notts, United Kingdom

[21] Appl. No.: 672,232

[22] Filed: Jul. 22, 1996

Related U.S. Application Data

[63] Continuation of Ser. No. 331,504, filed as PCT/EP93/01277, May 17, 1993 published as WO93/24103, Dec. 9, 1993, abandoned.

[30] Foreign Application Priority Data

May 22, 1992 [GB] United Kingdom .................. 9210947

[51] Int. Cl.$^6$ .............................. A61K 7/16; A61K 7/18; A61K 7/22; A61K 31/28
[52] U.S. Cl. .................. 424/49; 424/48; 424/52; 424/53; 424/54; 424/440; 424/421; 424/464; 424/468; 424/489; 424/600; 424/604; 424/606; 424/617; 424/618; 424/630; 424/635; 424/641; 424/642; 424/643; 424/649; 424/650; 424/688; 424/691
[58] Field of Search ................... 424/49, 52, 54, 424/604, 606, 617–618, 630, 635, 641, 642, 649, 688, 691, 48, 440, 421, 53, 600, 643, 650, 464, 468, 489

[56] References Cited

U.S. PATENT DOCUMENTS 5,180,585  1/1993  Jacobson et al. .................. 424/405

OTHER PUBLICATIONS

The Boots Company, Development Department (BCM) Report No. 373 Dec. 14, 1992.
The Boots Company, Development Department (BCM) Report No. DD377 Mar. 3, 1993.
The Boots Company, Development Department (BCM) Report No. 488 Oct. 27, 1994.
JP 03002113A (Jan. 8, 1991) Sanpo Seiyaku (Ogawara).
EP 251783A (Jan. 7, 1988) Edwards et al (Johnson Matthey).
JP 03127708 A2 (May 30 1991) Kioshi et al(Koa Glass).
EP 345116 A1 (Dec. 6, 1989) PLR Sello (Rhine–Poulenc).
EP Z97563A2 (Jan. 04 1989) Gioffre et al (Union Carbide).
USSR SU 1159575 A1 (Jun. 7, 1985) Kodola et al/Chuiko, et al.
CZECH CS 136064 (Apr. 15, 1970) Spinka.
JP 01238508 A (Sep. 22, 1989) Dewtal Chem Ltd.

*Primary Examiner*—John Pak
*Attorney, Agent, or Firm*—Nikaido Marmelstein Murray & Oram LLP

[57]  ABSTRACT

An oral hygiene composition comprises an effective amount of an antimicrobial agent in the form of a particulate non-ion-exchanging support material combined with a metal source providing antimicrobial metal ions in use. Preferably the antimicrobial agent is particulate titanium dioxide coated with silver chloride.

20 Claims, No Drawings

ORAL HYGIENE COMPOSITION

This application is a continuation of application Ser. No. 08/331,504 filed Jan. 27, 1995, now abandoned, which is a National Stage Entry of PCT application Ser. No. PCT/EP93/01277, May 17, 1993 published as WO93/24103, Dec. 9, 1993.

The present invention relates to an oral hygiene composition providing sustained antimicrobial action. There is also provided inter alia the use of such a composition in the treatment or prevention of dental caries or gingivitis and in the cleansing of the mouth for cosmetic purposes.

The term 'oral hygiene composition' as used herein indicates a formulation for use in any form of oral hygiene or dental treatment and includes inter alia dentifrices, mouthwashes, toothpowders, chewing gums, lozenges, mouthsprays, flosses, denture cleansing formulations, tooth paints and glass ionomer cements.

The use of antimicrobial agents in oral hygiene compositions is well-known in the art. Typically, the anti-microbial agent is an organic species such as chlorhexidine, bromochlorophene, cetyl pyridinium chloride or benzethonium chloride. These agents are known to be effective against the microorganisms associated with dental caries and gingivitis, such as the bacteria *Streptococcus mutans* and *Streptococcus salivarius*, and the fungus *Candida albicans*.

It is also known to use metal ions, such as silver, copper and zinc ions, as antimicrobial agents in medicine, dentistry and in water purification.

In an oral composition, however, such organic and inorganic antimicrobial agents present the problem that they are readily displaced from the mouth, and thus from their intended point of action. For example, they may be washed out of the mouth by saliva or adsorbed onto food at mealtimes. Accordingly, their oral antimicrobial action can rarely be sustained over long periods.

The present invention seeks to solve this problem by providing an oral composition comprising an antimicrobial agent with a tendency to remain in the mouth in use, thus giving sustained antimicrobial activity and enhanced protection against dental caries and gingivitis.

JP-A-03002113 (Sanpo Seijaku KK) discloses a dentifrice comprising an antimicrobial metal, such as copper, silver or zinc, carried on a zeolite. The dentifrice is stated to be storage-stable.

JP-A-02283312 (Sanpo Seijaku KK) discloses a toothbrush having brush-hairs incorporating a bactericidal metal-carrying zeolite, the metal being carried on the zeolite by ion-exchange. The toothbrush is used for brushing teeth and gums.

EP-A-0251783 (Johnson Matthey PLC) discloses an antimicrobial composition comprising an antimicrobial silver compound deposited on a physiologically inert oxidic synthetic material. The synthetic material is particulate, has an extended surface area, and may be selected from oxides of titanium, magnesium, aluminium, silicon, cerium, zirconium, hafnium, niobium and tantalum as well as calcium hydroxyapatite and barium sulphate. The antimicrobial compound is described as being suitable for topical use, for impregnation of fibrous or absorbent substrates such as bandages or wound-dressings or for impregnation into medical appliances such as catheters.

It has now surprisingly been found that antimicrobial agents of the type disclosed in EP-A-0251783 are particularly well-suited to use in oral hygiene compositions. The agents in question show a high degree of substantivity to the mouth, and to the teeth and gums in particular, thus providing sustained oral antimicrobial action.

According to the present invention there is provided an oral hygiene composition comprising an effective amount of an antimicrobial agent in the form of a particulate non-ion-exchanging support material combined with a metal source providing antimicrobial metal ions in use.

Preferably, the metal source is a metal compound, preferably a very sparingly soluble metal salt, suitably a silver salt such as silver chloride, since silver ions show particularly effective antimicrobial action. However, other antimicrobial metals such as copper, gold, platinum and zinc may also be used to good effect. The support material is preferably an inert oxide, preferably an inert metal oxide such as titanium dioxide (preferably in one or more of the crystalline forms anatase, rutile or brookite, suitably rutile) aluminium oxide, zirconium oxide or magnesium oxide.

Suitably, such antimicrobial agents may be prepared by suspending the support material in an aqueous solution of a soluble metal compound and reacting this suspension with a compound containing the anion of a desired antimicrobial metal salt. For example, titanium dioxide may be suspended in an aqueous solution of silver nitrate and reacted with silver chloride to precipitate silver chloride on the titanium dioxide. An example of this process is described in EP-A-0251783 (Johnson Matthey PLC) which is herein incorporated by way of reference.

Photographic evidence shows that such antimicrobial agents have a high degree of substantivity to the mouth, and tests show that they provide an effective supply of antimicrobial silver ions in use. The agent has particular affinity for carious lesions, cavities and dentinal tubules. The accumulation of the antimicrobial agent in these regions provides a high local concentration of antimicrobial silver ions whilst allowing the overall concentration of such ions in the mouth to be kept quite low, as required to remove any risk of toxicity to the user. The antimicrobial metal ions are thus concentrated where they are needed most, in the carious lesions, cavities and dentinal tubules where the risk of microbially induced decay is greatest.

The antimicrobial agent may be employed alone or in combination with further antimicrobial agents, for instance zinc salts such as zinc citrate and tin salts such as stannous fluoride or stannous pyrophosphate, and organic antimicrobial agents such as bromochlorophene, triclosan and cetyl pyridinium chloride. The latter agents provide excellent short-term antimicrobial action which is, in many respects, complementary to the longer-term action provided by the antimicrobial agents of the present invention.

The antimicrobial metal source may be present in an amount of from 0.5 to 75% by weight of the antimicrobial agent as a whole. Suitably, the amount of the metal source is from 1 to 50%, preferably from 2 to 25% by weight of the antimicrobial agent. The latter range provides a good compromise between the need to provide an antimicrobially effective concentration of free antimicrobial metal ions in use, and the need to keep levels of metal ions low to remove any risk of toxicity and to keep down costs.

Preferably, the particulate support material has an average particle size of less than 25 micrometers. Suitably, the particle size is between 0.01 and 15 micrometers. Suitably the particles have an open morphology. Preferably each particle comprises an agglomeration of crystallites having open spaces between the crystallites. Suitably the particles are roughly spherical clusters of crystallites. Preferably the particles exhibit some irregularity of shape. Where titanium dioxide is used to provide the crystallites, the primary crystal size will preferably be between 0.005 micrometers and 5 micrometers, preferably between 0.01 micrometer and 1 micrometer, thus allowing the antimicrobial agent to accumulate in carious lesions, cavities and dentinal tubules in use.

Preferably, the support material has a mean surface area of from 1 to 300 m²/g. It will be understood that a high surface area may be required to support the necessary amount of antimicrobial metal compound, which should preferably be dispersed thinly on the support so as to maximise availability in use.

Suitably, the antimicrobial agent may be included in the oral composition in an amount of from $1\times10^{-5}$ to 5% by weight, preferably from 0.01% to 3% by weight.

The oral composition may be formulated for use in any form of interdental or periodontal treatment and may be in the form, for example, of a dentifrice, mouthwash, toothpowder, chewing gum, lozenge, mouthspray, floss, dental paint, or glass ionomer cement. Use of the antimicrobial material of the present invention in a glass ionomer cement has the advantage of providing X-ray opacity as well as antimicrobial action.

Such compositions may, as appropriate, contain conventional materials such as, for example, humectants, surfactants, gelling agents, abrasives, fluoride sources, desensitising agents, flavourings, colourings, sweeteners, preservatives, structuring agents, bactericides, anti-tartar agents and anti-plaque agents.

Suitable humectants for use in dentifrice compositions include polyhydric alcohols such as xylitol, sorbitol, glycerol, propylene glycol and polyethylene glycols. Mixtures of glycerol and sorbitol are particularly effective. A humectant helps to prevent dentifrice compositions from hardening on exposure to air, and may also provide a moist feel, smooth texture, flowability, and a desirable sweetness in the mouth. Suitably, such humectants may comprise from about 0–85%, preferably from about 0–60% by weight of the oral hygiene composition.

Suitable surfactants for use in dentifrices, mouthwashes etc. are usually water-soluble organic compounds, and may be anionic, nonionic, cationic or amphoteric species. The surfactant used should preferably be reasonably stable, able to form suds throughout a wide pH range, and able to produce a foam in use.

Anionic surfactants include the water-soluble salts of $C_{10-18}$ alkyl sulphates (e.g. sodium lauryl sulfates), water soluble salts of $C_{10-18}$ ethoxylated alkyl sulphates, water soluble salts of $C_{10-18}$ alkyl sarcosinates, the water-soluble salts of sulfonated monoglycerides of $C_{10-18}$ fatty acids (e.g. sodium coconut monoglyceride sulfonates), alkyl aryl sulfonates (e.g. sodium dodecyl benzene sulfonate) and sodium salts of the coconut fatty acid amide of N-methyltaurine.

Nonionic surfactants suitable for use in oral compositions include the products of the condensation of alkylene oxide groups with aliphatic or alkylaromatic species, and may be for example, polyethylene oxide condensates of alkyl phenols, ethylene oxide/propylene oxide copolymers (available from BASF Wyandotte Chemical Corporation under the trade name 'Pluronic'), ethylene oxide/ethylene diamine copolymers, ethylene oxide condensates of aliphatic alcohols, long chain tertiary amine oxides, long chain tertiary phosphine oxides, long chain dialkyl sulfoxides and mixtures thereof. Alternatives include ethoxylated sorbitan esters such as those available from ICI under the trade name "Tween".

Cationic surfactants are generally quaternary ammonium compounds having one $C_{8-18}$ alkyl chain and include, for example, lauryl trimethylammonium chloride, cetyl trimethylammonium bromide, cetyl pyridinium chloride, di-isobutylphenoxyethoxyethyldimethylbenzylammonium chloride, coconutalkyltrimethylammonium nitrite and cetyl pyridinium fluoride. Also useful are benzyl ammonium chloride, benzyl dimethyl stearylammonium chloride, and tertiary amines having one $C_{1-18}$ hydrocarbon group and two (poly)oxyethylene groups.

Amphoteric surfactants are generally aliphatic secondary and tertiary amines comprising aliphatic species which may be branched or unbranched, and in which one of the aliphatic species is a $C_{8-18}$ species and the other contains an anionic hydrophilic group, for example, sulfonate, carboxylate, sulfate, phosphonate or phosphate. Examples of quaternary ammonium compounds are the quaternized imidazole derivatives available under the trade name 'Miranol' from the Miranol Chemical Company.

Suitably, the surfactant is included in an amount of from 0–20%, preferably 0–10% by weight of the oral hygiene composition.

Structuring agents may be required in, for example, dentifrices and gums to provide desirable textural properties and "mouthfeel". Suitable agents include natural gum binders such as gum tragacanth, xanthan gum, gum karaya and gum arabic, seaweed derivatives such as Irish moss and alginates, smectite clays such as bentonite or hectorite, carboxyvinyl polymers and water-soluble cellulose derivatives such as hydroxyethyl cellulose and sodium carboxymethyl cellulose. Improved texture may also be achieved, for example, by including colloidal magnesium aluminium silicate. Suitably, the structuring agent is included in an amount of from 0–5%, preferably 0–3% by weight of the oral hygiene composition.

Abrasives should preferably be capable of cleaning and/or polishing the teeth without causing harm to dental enamel or dentine. They are used most commonly in dentifrices and toothpowders, but may also be used in mouthwashes etc. Suitable abrasives include the silica abrasives, such as hydrated silicas and silica gels, particularly silica xerogels such as those available under the trade name 'Syloid' from W. R. Grace and Company. Also suitable are precipitated silica materials such as those available under the trade name 'Zeodent' from J. M. Huber Corporation, and diatomaceous earths such as those available under the trade name 'Celite' from Johns-Manville Corporation. Alternative abrasives include alumina, insoluble metaphosphates such as insoluble sodium metaphosphate, calcium carbonate, dicalcium phosphate (in dihydrate and anhydrous forms), calcium pyrophosphate (including β-phase calcium) polymethoxylates and particulate thermosetting polymerised resins such as, for example, melamine-ureas, melamine-formaldehydes, urea-formaldehydes, melamine-urea-formaldehydes, cross-linked epoxides, melamines, phenolics, highly purified celluloses such as those available under the trade name 'Elcema' from Degussa AG, and cross-linked polyesters. Suitably, abrasives are included in an amount of from 0–80%, preferably 0–60% by weight of the oral hygiene composition.

Fluoride sources suitable for use in all oral hygiene compositions of the present invention include sodium fluoride, zinc fluoride, potassium fluoride, aluminium fluoride, lithium fluoride, sodium monofluorophosphate, acidulated phosphate fluoride, stannous fluoride, ammonium fluoride, ammonium bifluoride and amine fluoride.

Preferably, the fluoride source is present in an amount sufficient to provide from about 50 ppm to about 4,000 ppm fluoride ions in use. Inclusion of a fluoride source is beneficial, since fluoride ions are known to become incorporated into the hydroxyapatite of tooth enamel, thereby increasing the resistance of the enamel to decay. Fluoride is also now thought to act locally on the tooth enamel, altering the remineralisation-demineralisation balance in favour of reminderalisation. Inclusion of a fluoride source is also desirable when a polyphosphate anti-calculus agent is included, in order to inhibit the enzymic hydrolysis of such polyphosphates by salivary phosphatase enzymes.

Suitable desensitising agents include, for example, formaldehyde, potassium nitrate, tripotassium citrate, potassium chloride and strontium chloride (suitably as hexahydrate), strontium acetate (suitably as hemihydrate) and sodium citrate/Pluronic gel.

Flavouring agents may be added to increase palatability and may include, for example, oils of peppermint, spearmint, wintergreen, sassafras and clove. Sweetening agents may also be used, and these include D-tryptophan, saccharin, dextrose, aspartame, levulose, acesulfam, dihydrochalcones and sodium cyclamate. Typically, such flavouring agents are included in amounts of from 0–5%, preferably from 0–2% by weight of the oral hygiene composition. Colouring agents and pigments may be added to improve the visual appeal of the composition. Suitable colourants include dyes, such as FD & C blue No.1, D & C yellow No.10 and D & C yellow No.3. A suitable and commonly used pigment is pigment grade titanium dioxide, which provides a strong white colour.

Suitably, as described above, the compositions of the invention may include a further antimicrobial agent as a preservative and/or anti-plaque agent. Suitable antimicrobial agents include zinc salts (such as zinc citrate), cetyl pyridinium chloride, the bis-biguanides (such as chlorhexidine), aliphatic amines, bromochlorophene, hexachlorophene, salicylanilides, quaternary ammonium compounds and triclosan. Enzymic systems providing a source of a natural biocide may be used as alternatives to or in combination with the biocides listed. For example, a system comprising lactoperoxidase and glucose oxidase may be used to generate antimicrobial amounts of hydrogen peroxide in the presence of glucose, water and oxygen.

The composition may also comprise an anti-calculus agent. Suitable anti-calculus agents include zinc salts such as zinc citrate and zinc chloride and polyphosphates. Suitable pyrophosphates include the sodium and potassium pyrophosphates, preferably disodium pyrophosphate, dipotassium pyrophosphate, tetrasodium pyrophosphate and tetrapotassium pyrophosphate. A preferred source of pyrophosphate is a mixture of tetrasodium pyrophosphate and tetrapotassium pyrophosphate. Suitably, the ratio of tetrasodium pyrophosphate to tetrapotassium pyrophosphate is 0:1 to 3:1, preferably 0:1 to 1:1. Preferably, tetrapotassium pyrophosphate is the predominant species.

The composition may also comprise alcohol. This component is particularly useful in mouthwash formulations, where it may be used to solubilise components which have low solubility in water.

Particularly suitable oral compositions are those in the form of a mouthwash or toothpaste.

According to a further aspect of the invention, there is provided a method of cleaning the mouth for cosmetic purposes by oral application of any oral hygiene composition as defined above.

In a further aspect, the invention provides a method of treating or preventing dental caries or gingivitis by oral application of any oral hygiene composition as defined above.

In a further aspect, there is provided the use of any anti-microbial agent as defined above in the treatment or prevention of dental caries or gingivitis.

In a still further aspect, there is provided the use of any anti-microbial agent as defined above in the manufacture of a medicament for the treatment or prevention of dental caries or gingivitis.

The invention also provides the use of an antimicrobial agent as defined above to provide sustained antimicrobial activity in the mouth.

The nature of the present invention is illustrated by the following Tests and Examples.

EXAMPLE 1 (preparative)

A sample of an antimicrobial agent for use in the present invention is prepared substantially as described in EP-A-0251783 (Johnson Matthey PLC).

3.55 g of silver nitrate is dissolved in 400 ml of water at 80° C. 97 g of a suitable form of particulate titanium dioxide (having a mean crystallite size of about 250 nm) is dispersed into this solution. 1.4 g of sodium chloride (a slight excess) is dissolved in 100 ml of water at 80° C., The sodium chloride solution is then slowly added to the silver nitrate/titanium dioxide suspension with constant stirring. Stirring at a temperature of 80° C. is maintained far two hours with light excluded. The temperature is then lowered to 20° C. and stirring continued for a further hour (still excluding light). The suspension is filtered and the silver chloride coated titanium dioxide thus produced is dried and milled, yielding a free-flowing powder containing about 3% silver chloride by weight, Comparative Test A An antimicrobial agent prepared substantially as described in Example 1 was tested for antimicrobial activity against *Streptococcus salivarius* and *Streptococcus mutans*, which are organisms known to be associated with dental caries/gingivitis and against *Candida albicans*.

A sample of silver chloride coated titanium dioxide was prepared substantially as described in EP-A-0251783 (acknowledged above). The sample was found to have a silver chloride content (as measured by strong acid extraction) of 2.07%, a sodium content of 0.32% and a titanium dioxide content (determined through the residue from acid extraction) of 83.6%

Using standard microbiological methods, this sample was placed on an agar plate loaded with test organism. Plates were incubated at 37° C. for 48 hours and examined at 24 hours and 48 hours for microbial growth inhibition. By including the sample at different concentrations it was possible to calculate the minimum inhibitory concentration (MIC) against each organism.

Corresponding tests were carried out on untreated titanium dioxide BP, as a control. Results are shown in Table 1. Where a second figure is shown in the table, this indicates that a different MIC (as shown) was obtained at 48 hours.

TABLE 1

| | MIC (ppm) | |
|---|---|---|
| Organism | Untreated TiO$_2$ (control) | AgCl/TiO$_2$ (from Example 1) |
| S. Salivarius (NCB 8883) | >10,000 | 312  (2,500) |
| S. Mutans (NCTC 10449) | >10,000 | 312  (2,500) |
| C. Albicans (PHL 239) | >10,000 | 5,000 |

These results show the activity of the antimicrobial agent of the present invention against organisms known to be associated with dental caries/gingivitis. It will be noted that activity was not detected in the control.

As noted by Richie and Jones, in Letters in Applied Microbiology (1990) 11, 152–154, the activity shown by the agent of the present invention is probably an underestimate of true activity because of the tendency of agar and of cysteine and hemin in the culture medium to bind or complex free silver ions. Accordingly, it is to be expected that antimicrobial activity would be considerably greater in vivo.

Comparative Test B

The anti-plaque activity of the compositions according to the present invention has been demonstrated as follows. Thin strips of aluminium were used as "artificial tooth" surfaces on which plaque, collected from a small number of donors, was grown. Growth was encouraged by the provision of conditions resembling a normal oral environment (saliva, nutrients, pH and temperature) over a two day period with simulations made of the intake of two meals and of a sleeping, low nutrient period. The aluminium strips (and plaque) were exposed for one minute on two occasions to a suspension of the composition to be tested with distilled water and fresh saliva, thus simulating evening and morning toothbrushing sessions. Following the second exposure, plaque remaining on the strips after a four hour growth period and subsequent rinsing was dispersed by ultrasonic vibration. The optical density of the resulting plaque suspensions at 570 nm (two replicate readings per strip) was used to estimate the percentage reduction in plaque growth compared to plaque growth on test strips exposed to a control composition of saliva and water.

The test compared a 1% suspension of the silver chloride coated titanium .dioxide antimicrobial agent (from Test A) with a 1% suspension of uncoated titanium dioxide as a control.

The mean optical density value obtained in this test with samples treated with the antimicrobial agent of the present invention was 0.041±0.013. In contrast, the corresponding mean value obtained with control samples (treated only with uncoated titanium dioxide) was 0.110±0.013.

These results clearly show the antimicrobial effect of the antimicrobial agent of the present invention in a simulated oral environment.

Comparative Test C Human plaque collected from a small number of donors was used to inoculate three different growth media (1, 2 and 3) made up as follows:

Medium 1

| Component | Concentration (g/l) |
|---|---|
| Tryptone | 20 |
| Yeast extract | 5 |
| $K_2HPO_4$ | 4 |
| $KH_2PO_4$ | 1 |
| $MgCl_2$ | 0.0132 |
| $CaCl_2$ | 0.016 |
| $MnCl_2$ | 0.00036 |

(pH adjusted to 6.8 with HCl)

Medium 2

| Component | Concentration (g/l) |
|---|---|
| $CaCl_2$ | 0.229 |
| $MgCl_2$ | 0.0403 |
| NaCl | 0.257 |
| NaSCN | 0.105 |
| NaF | 0.00063 |
| KI | 0.00013 |
| $KHCO_3$ | 0.5005 |
| $NaHCO_3$ | 1.68 |
| $KH_2PO_4$ | 0.816 |
| KCl | 0.7455 |
| Urea | 0.193 |
| Glucose | 0.099 |
| Lactoferrin | 0.0054 |
| Lysozyme | 0.132 |
| α-amylase | 0.38 |
| Lactoperoxidase | 0.002 |
| Albumin | 2.2028 |

Medium 3

| Component | Concentration (g/l) |
|---|---|
| Tryptone | 20 |
| Yeast extract | 5 |
| $CaCl_2$ | 0.229 |
| $MgCl_2$ | 0.0403 |
| NaCl | 0.257 |
| NaSCN | 0.105 |
| NaF | 0.00063 |
| KI | 0.00013 |
| $KHCO_3$ | 0.5005 |
| $NaHCO_3$ | 1.68 |
| $KH_2PO_4$ | 0.816 |
| KCl | 0.7455 |
| Urea | 0.193 |
| Glucose | 0.099 |
| Lactoferrin | 0.0054 |
| Lysozyme | 0.132 |
| α-amylase | 0.38 |
| Lactoperoxidase | 0.002 |
| Albumin | 2.2028 |

Each culture (14.35 ml for test solutions, 14.5 ml for controls) was incubated at 37° C. for up to 24 hours. After 2 hours incubation, each culture was "fed" a 30% sucrose solution (0.5 ml). At the same time a 1% suspension of silver chloride coated titanium dioxide (from Test A) was added to each test solution (but not to controls) to a final concentration of $1\times10^{-4}$%.

Optical density (OD; 570 nm) and pH measurements were made at hourly intervals throughout the incubation period on all cultures. Results are shown in Table 2.

TABLE 2

| | Test Solution (antimicrobial agent added at 2 hours) | Control (no antimicrobial agent added) |
|---|---|---|
| Medium 1 | | |
| pH after 6 hours | 6.69 | 4.44 |
| pH after 24 hours | 4.34 | 4.10 |
| OD after 6 hours | 0.425 | 1.74 |
| OD after 24 hours | 0.639 | 2.092 |
| Medium 2 | | |
| pH after 6 hours | 7.9 | 7.51 |
| pH after 24 hours | 7.83 | 4.73 |
| OD after 6 hours | 0.434 | 0.428 |
| OD after 24 hours | 0.32 | 1.072 |

TABLE 2-continued

| | Test Solution (antimicrobial agent added at 2 hours) | Control (no antimicrobial agent added) |
|---|---|---|
| Medium 3 | | |
| pH after 6 hours | 6.91 | 4.45 |
| pH after 24 hours | 6.64 | 4.21 |
| OD after 6 hours | 0.442 | 1.903 |
| OD after 24 hours | 0.4 | 2.162 |

Lower optical densities indicate lower microbial growth. Thus, these results show inhibition of bacterial growth (and associated prevention of reduction in pH in culture media) by use of an antimicrobial agent in accordance with the present invention. Antimicrobial action persisted for at least 24 hours.

FORMULATION EXAMPLE 1

Toothpaste

A toothpaste is prepared in conventional manner to the following composition:

| | % w/w |
|---|---|
| Sorbitol 70% solution (non-crystalline) | 50 |
| Toothpaste silica - abrasive Zeodent 113 | 12.22 |
| Toothpaste silica - thickener Zeodent 163 | 9.44 |
| Sodium fluoride BP | 0.26 |
| Sodium hydroxide BP pellet | 0.1 |
| Sodium lauryl sulphate and sodium sulphate (available under the trade name Empicol LZ PDR) | 1.5 |
| Titanium dioxide PH EUR | 0.75 |
| Sodium saccharin BP cryst | 0.26 |
| Sodium carboxymethylcellulose for toothpaste | 0.9 |
| Toothpaste flavour (% by volume) | 1.2 |
| Silver chloride coated titanium dioxide (as described in Test A) | 0.1 |
| Purified water BP | to 100 |

FORMULATION EXAMPLE 2

Mouthwash

A mouthwash is prepared in conventional manner to the following composition:

| | % w/w |
|---|---|
| Sorbitol 70% solution (non-crystalline) | 5 |
| Ethanol 96% BP (% by volume) | 7 |
| Sodium saccharin BP Cryst (76% Sac) | 0.02 |
| Polyethylene glycol-40 hydrogenated castor oil (available under the trade name Croduret 40 ET 0080 DF) | 0.15 |
| Polyoxyethylene sorbitan monolaurate (available under the trade name Tween 20) | 0.15 |
| Sodium fluoride BP | 0.05 |
| Sodium benzoate BP | 0.1 |
| Blue 12401 Anst | 0.0006 |
| Yellow 2G Anst | 0.00055 |
| Bentonite BP | 1 |
| Mouth rinse flavour (% by volume) | 0.1 |
| Silver chloride coated titanium dioxide (as described in Test A) | 0.5 |
| Purified water BP | to 100 |

FORMULATION EXAMPLE 3

Chewable lozenge

A chewable lozenge is prepared in conventional manner to the following composition:

| | % w/w |
|---|---|
| A. Hydrogenated glucose syrup (available under the trade name Lycasin 80/55) | 30.0 |
| Pectin (extra slow set, high-methoxy) | 0.6 |
| Sorbitol powder (available under the trade name Neosorb) | 2.0 |
| Carrageenan | 0.2 |
| Water | 66.1 |
| B. Citric acid | 0.3 |
| Water | 0.3 |
| Flavour/colour | 0.4 |
| Silver chloride coated titanium dioxide (as described in Test A) | 0.004 |

FORMULATION EXAMPLE 4

Chewable tablet (general formulation)

A chewable tablet is prepared in conventional manner to the following composition:

| | % w/w |
|---|---|
| Sorbitol (available under the Trade Name Sorbit Instant) | 96.9 |
| Flavour | q.s. |
| Colour | q.s. |
| Magnesium stearate (0.5%) | 0.5 |
| Silicon dioxide (0.1%) | 0.1 |
| Silver chloride coated titanium dioxide (as described in Test A) | 2.5 |

FORMULATION EXAMPLE 5

Antimicrobial tooth paint base

A tooth paint base is prepared in conventional manner to the following composition:

| | % w/w |
|---|---|
| Carboxylated polyacrylate (available under the trade name Surcol 836W) | 10.0 |
| Cellulose acetate | 1.0 |
| Ethanol (96% BP) | 88.0 |
| Silver chloride coated titanium dioxide (as described in Test A) | 1.0 |

FORMULATION EXAMPLE 6

Chewing gum base

A chewing gum base is prepared in conventional manner to the following composition:

| | % w/w |
|---|---|
| Latex (60%) | 18.0 |
| Hydrogenated Rosin Ester | 44.0 |
| Paracumarone ester | 7.5 |
| Candellila Wax | 6.0 |
| Glyceryl tristearate | 2.5 |
| Ethyl cellulose | 2.0 |
| Calcium carbonate | 19.9 |

-continued

| | % w/w |
|---|---|
| Silver chloride coated titanium dioxide (as described in Test A) | 0.1 |

We claim:

1. An oral composition suitable for use in oral hygiene or dental treatment comprising an effective amount of an antimicrobial agent in the form of a particulate, non-ion-exchanging, zeolite-free, inert metal oxide, a sparingly soluble metal salt providing antimicrobial metal ions in use and a further material selected from the group consisting of humectants, gelling agents, abrasives, fluoride sources, desensitizing agents, flavorings, colorings, sweeteners, preservatives, structuring agents, bactericides, anti-tartar agents and anti-plaque agents.

2. A composition as claimed in claim 1, wherein the metal salt is selected from the group consisting of silver, copper, gold, platinum and zinc salts.

3. A composition as claimed in claim 1, wherein the metal oxide is selected from the group consisting of titanium dioxide, aluminum oxide, zirconium oxide, hafnium oxide, niobium oxide, tantalum oxide, calcium hydroxyapatite, barium sulphate, and magnesium oxide.

4. A composition as claimed in claim 3, wherein the titanium dioxide is in at least one of anatase, rutile and brookite crystalline form.

5. A composition as claimed in claim 1 wherein the antimicrobial agent is employed in combination with a further antimicrobial agent providing short-term antimicrobial action.

6. A composition as claimed in claim 1 wherein the metal salt is present in an amount of from about 0.5 to 75% by weight of the antimicrobial agent.

7. A composition as claimed in claim 6 wherein the metal salt is present in an amount of from about 1 to 50% by weight of the antimicrobial agent.

8. A composition as claimed in claim 7 wherein the metal salt is present in an amount of from about 2 to 25% by weight of the antimicrobial agent.

9. A composition as claimed in claim 1 wherein the metal oxide has an average particle size of less than about 25 micrometers.

10. A composition as claimed in claim 9 wherein the average particle size is between about 0.01 and 15 micrometers.

11. A composition as claimed in claim 1 wherein the metal oxide is titanium dioxide having a primary crystal size of from about 0.005 to 5 micrometers.

12. A composition as claimed in claim 11 wherein the titanium dioxide has a primary crystal size of from about 0.01 to 1 micrometers.

13. A composition as claimed in claim 1 wherein the metal oxide has a mean surface area of from about 1 to 300 $m^2/g$.

14. A composition as claimed in claim 1 wherein the antimicrobial agent is included in the composition in an amount of from about $1 \times 10^{-5}$ to 5% by weight.

15. A composition as claimed in claim 14 wherein the antimicrobial agent is included in the composition in an amount of from about 0.01% to 3% by weight.

16. A method of cleaning a mouth of an individual for cosmetic purposes, comprising applying to the mouth an oral hygiene composition comprising an effective amount of an antimicrobial agent comprising a particulate, non-ion-exchanging, zeolite-free, inert metal oxide and a sparingly soluble metal salt providing antimicrobial metal ions in use.

17. A method of treating or preventing dental caries or gingivitis, comprising applying to a mouth of an individual an oral hygiene composition comprising an effective amount of an antimicrobial agent comprising a particulate, non-ion-exchanging, zeolite-free, inert metal oxide and a sparingly soluble metal salt providing antimicrobial metal ions in use.

18. A method of providing sustained antimicrobial activity in a mouth of an individual, comprising applying to the mouth an oral hygiene composition comprising an effective amount of an antimicrobial agent comprising a particulate, non-ion-exchanging, zeolite-free, inert metal oxide and a sparingly soluble metal salt providing antimicrobial metal ions in use.

19. A composition as claimed in claim 5, wherein the further antimicrobial agent is selected from the group consisting of a zinc salt, a tin salt, cetyl pyridinium chloride, a bis-biguanide, aliphatic amines, bromochlorophene, hexachlorophene, salicylanilides, a quarternary ammonium compound and triclosan.

20. A composition as claimed in claim 1, wherein the composition is selected from the group consisting of a dentrifice, mouthwash, tooth powder, chewing gum, lozenge, mouth spray, denture cleansing formulation, tooth paint and glass ionomer cement.

* * * * *